(12) United States Patent
Ohnishi et al.

(10) Patent No.: US 8,241,227 B2
(45) Date of Patent: Aug. 14, 2012

(54) BIOPSY TISSUE SAMPLING TREATMENT INSTRUMENT

(75) Inventors: Junichi Ohnishi, Hachioji (JP); Masatoshi Tonomura, Koganei (JP); Akira Suzuki, Uenohara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/845,262

(22) Filed: Jul. 28, 2010

(65) Prior Publication Data
US 2011/0105944 A1 May 5, 2011

Related U.S. Application Data

(63) Continuation of application No. PCT/JP2009/066801, filed on Sep. 28, 2009.

(30) Foreign Application Priority Data

Mar. 5, 2009 (JP) ................................. 2009-052366

(51) Int. Cl.
*A61B 10/00* (2006.01)
(52) U.S. Cl. ......... 600/567; 600/562; 600/564; 600/570
(58) Field of Classification Search .................. 600/562, 600/564–568
See application file for complete search history.

(56) References Cited

U.S. PATENT DOCUMENTS

| | | | | |
|---|---|---|---|---|
| 3,929,123 A | * | 12/1975 | Jamshidi | 600/567 |
| 4,142,517 A | * | 3/1979 | Contreras Guerrero de Stavropoulos et al. | 600/567 |
| 4,340,066 A | * | 7/1982 | Shah | 600/562 |
| 4,884,572 A | * | 12/1989 | Bays et al. | 606/139 |
| 5,368,046 A | * | 11/1994 | Scarfone et al. | 600/567 |

(Continued)

FOREIGN PATENT DOCUMENTS

JP   S48-74687   9/1973

(Continued)

OTHER PUBLICATIONS

Extended Supplementary European Search Report dated Mar. 22, 2012 issued in counterpart European Patent Application No. 09841140.8.

*Primary Examiner* — Max Hindenburg
*Assistant Examiner* — Adam Eiseman
(74) *Attorney, Agent, or Firm* — Scully, Scott, Murphy & Presser, P.C.

(57) ABSTRACT

A biopsy tissue sampling treatment instrument includes a stem portion having a predetermined length sufficient to puncture living tissue; a puncturing portion formed at a distal end of the stem portion and having a protruding surface portion expanding rearward along a puncture direction of the stem portion; a tissue holding surface provided on a rear side of the protruding surface portion in the puncturing portion and having an area large enough to hold the living tissue; a stopper member provided at a rear end of the stem portion and having an abutting portion capable of abutting against the living tissue punctured by the stem portion; and an operating member provided on the stopper member and configured to hold the stem portion to the living tissue, allowing the stem portion to puncture the living tissue. Consequently, the biopsy tissue sampling treatment instrument increases holding capacity for the living tissue to be extracted, allows living tissue to be extracted in sufficient sampling quantities, and makes it easy to take samples of living tissue at an intended depth in tissue.

13 Claims, 15 Drawing Sheets

U.S. PATENT DOCUMENTS

| | | | |
|---|---|---|---|
| 5,372,583 A * | 12/1994 | Roberts et al. | 604/506 |
| 5,456,267 A | 10/1995 | Stark | |
| 5,660,186 A | 8/1997 | Bachir | |
| 5,810,826 A * | 9/1998 | .ANG.kerfeldt et al. | 606/80 |
| 6,695,859 B1 | 2/2004 | Golden et al. | |
| 2002/0016556 A1 | 2/2002 | Williams | |
| 2004/0102797 A1 | 5/2004 | Golden et al. | |
| 2006/0036211 A1 | 2/2006 | Solsberg et al. | |
| 2006/0036271 A1 | 2/2006 | Schomer et al. | |
| 2006/0036272 A1 | 2/2006 | Solsberg et al. | |
| 2006/0184175 A1 | 8/2006 | Schomer et al. | |
| 2006/0206115 A1 | 9/2006 | Schomer et al. | |
| 2006/0235451 A1 | 10/2006 | Schomer et al. | |
| 2006/0235452 A1 | 10/2006 | Schomer et al. | |
| 2006/0264994 A1 | 11/2006 | Schomer et al. | |
| 2007/0198019 A1 | 8/2007 | Schomer et al. | |
| 2007/0213634 A1 * | 9/2007 | Teague | 600/564 |
| 2010/0317996 A1 * | 12/2010 | Dillon | 600/567 |

FOREIGN PATENT DOCUMENTS

| | | |
|---|---|---|
| JP | 05-015543 | 1/1993 |
| JP | 07-033305 | 6/1995 |
| JP | 07-039807 | 7/1995 |
| JP | 09-192135 | 7/1997 |
| JP | 2001-029349 | 2/2001 |
| JP | 2001-070307 | 3/2001 |
| JP | 2008-508058 A | 3/2008 |
| WO | WO 00/59380 A2 | 10/2000 |
| WO | WO 2006/015302 A1 | 2/2006 |

* cited by examiner

BIOPSY TISSUE SAMPLING TREATMENT INSTRUMENT

CROSS REFERENCE TO RELATED APPLICATION

This application is a continuation application of PCT/JP2009/066801 filed on Sep. 28, 2009 and claims benefit of Japanese Application No. 2009-052366 filed in Japan on Mar. 5, 2009, the entire contents of which are incorporated herein by this reference.

BACKGROUND OF THE INVENTION

1. Field of the Invention

The present invention relates to a biopsy tissue sampling treatment instrument which is inserted into the body of a patient and used to take samples of tissue in the body.

2. Description of the Related Art

In recent years, treatment instruments for transbronchially taking samples of living tissue have been widely used, for example, to carry out pre-treatment diagnosis of cell abnormalities using a bronchoscope. Such treatment instruments are disclosed, for example, in Japanese Patent Application Laid-Open Publication No. 2001-29349, Japanese Utility Model Application Laid-Open Publication No. 7-33305, Japanese Patent Application Laid-Open Publication No. 9-192135, and Japanese Patent Application Laid-Open Publication No. 5-15543.

Regarding treatment instruments generally used with endoscopes, wide use is made of endoscopic needle biopsy forceps equipped with a pair of opening-closing forceps cups such as disclosed in Japanese Patent Application Laid-Open Publication No. 2001-29349. In the conventional endoscopic needle biopsy forceps, a needle is disposed so as to protrude in a pair of forceps cups, and a thorn-like portion which protrudes obliquely backward is provided near a distal end of the needle.

Japanese Utility Model Application Laid-Open Publication No. 7-33305 discloses an endoscopic bacteria sampling brush or a so-called cytological brush which takes a sample of mucosae from a lumen of a living body by scratching a luminal wall of the living body with a protruding brush unit and causing the mucosae to adhere to the brush unit. Furthermore, Japanese Patent Application Laid-Open Publication No. 9-192135 discloses a cytological brush which takes a sample of living tissue using multiple flaps provided in a distal part of an operation sheath different in form from the brush unit disclosed in Japanese Utility Model Application Laid-Open Publication No. 7-33305.

Besides, Japanese Patent Application Laid-Open Publication No. 5-15543 discloses a cell sampling tool which includes a body piercing member equipped with a piercing head rotationally disposed at a flexible distal end, where a spiral cell sampling groove is formed in a suitable shape in the piercing head.

SUMMARY OF THE INVENTION

The present invention provides a biopsy tissue sampling treatment instrument including: a stem portion having a predetermined length sufficient to puncture living tissue; a puncturing portion formed at a distal end of the stem portion and having a protruding surface portion expanding rearward along a puncture direction of the stem portion; a tissue holding surface provided on a rear side of the protruding surface portion in the puncturing portion and having an area large enough to hold the living tissue; a stopper member provided at a rear end of the stem portion and having an abutting portion capable of abutting against the living tissue punctured by the stem portion; and an operating member provided on the stopper member and configured to hold the stem portion to the living tissue, allowing the stem portion to puncture the living tissue.

DETAILED DESCRIPTION OF THE PREFERRED EMBODIMENTS

Embodiments of the present invention will be described below with reference to the drawings. The description will be given taking as an example a biopsy tissue sampling treatment instrument which takes samples of living tissue via an endoscope used, for example, for transbronchial examinations and biopsies.

First Embodiment

Figure 1:
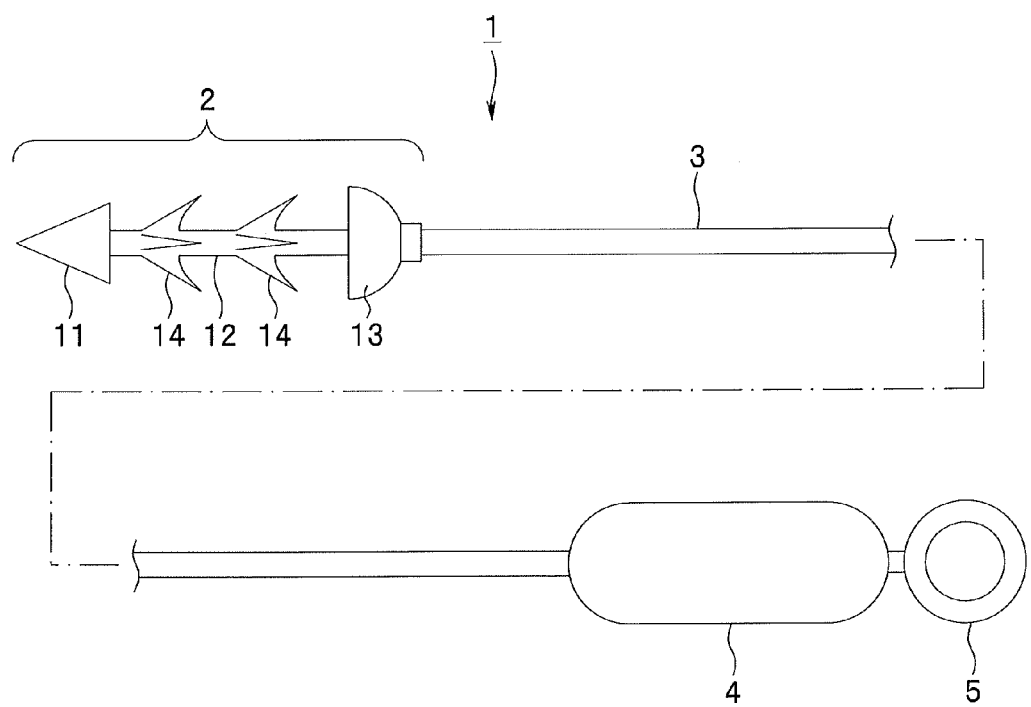
FIG. 1 is a diagram showing a configuration of a biopsy tissue sampling treatment instrument according to a first embodiment.
Figure 2:
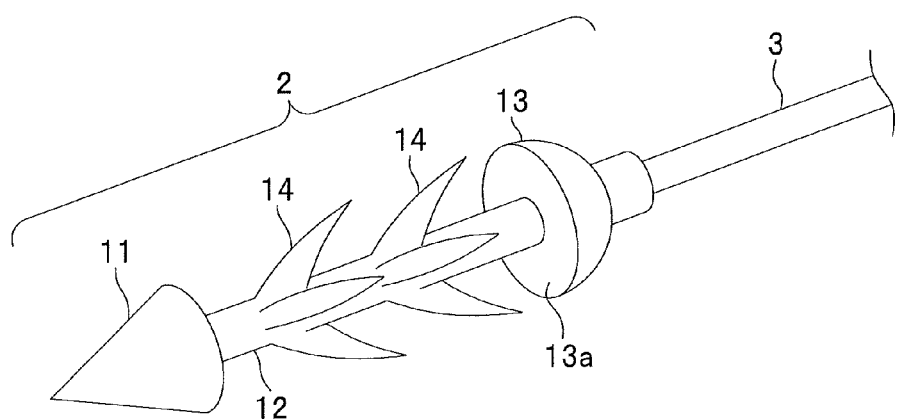
FIG. 2 is a perspective view showing a configuration of a tissue sampling unit according to the first embodiment.
Figure 3:
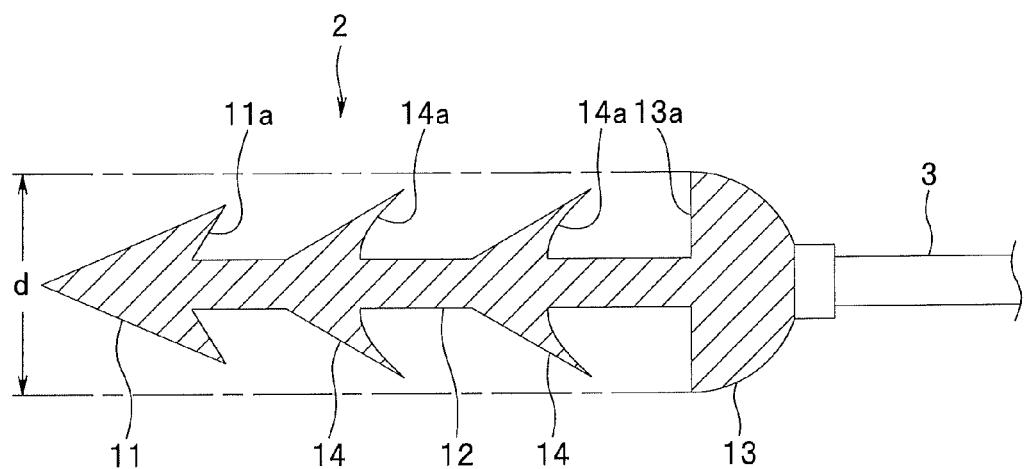
FIG. 3 is a sectional view showing the configuration of the tissue sampling unit according to the first embodiment.
Figure 4:
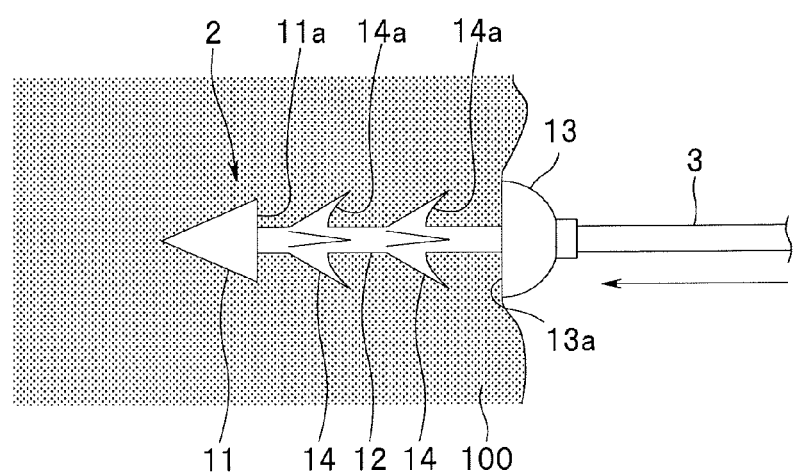
FIG. 4 is a sectional view showing how living tissue is punctured by the tissue sampling unit, according to the first embodiment.
Figure 5:
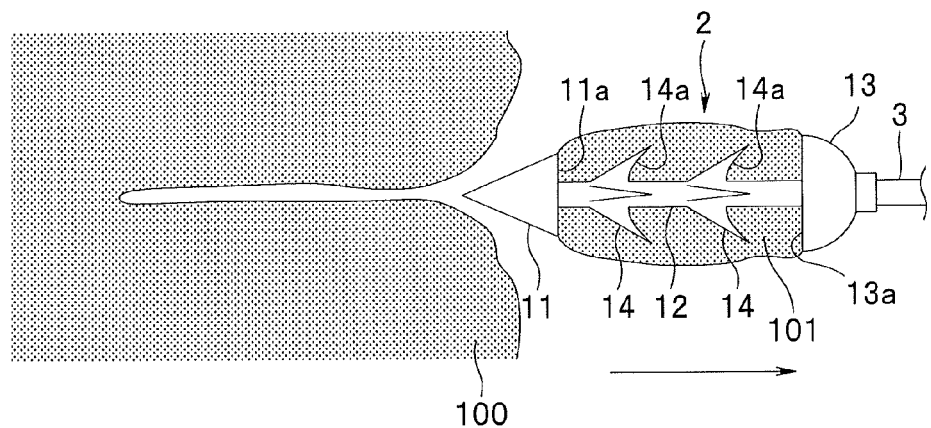
FIG. 5 is a sectional view showing how the tissue sampling unit is pulled out of the living tissue and tissue fragments scraped off are held by the tissue sampling unit, according to the first embodiment.
Figure 6:
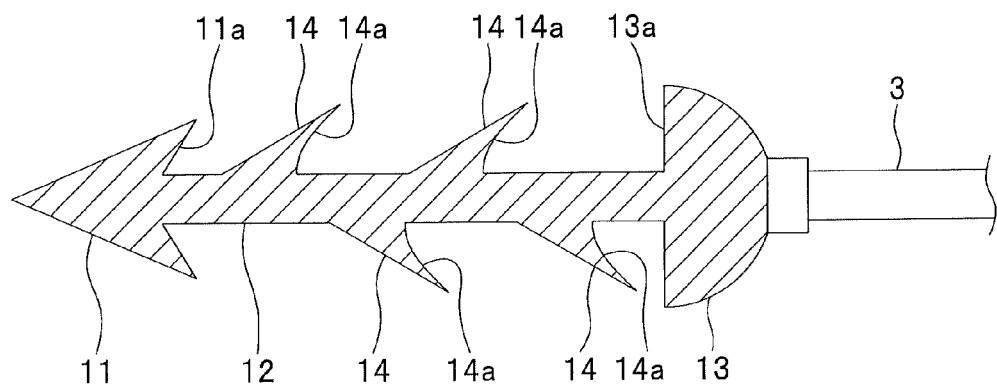
FIG. 6 is a sectional view showing a configuration of a tissue sampling unit according to a first variation of the first embodiment.
Figure 7:
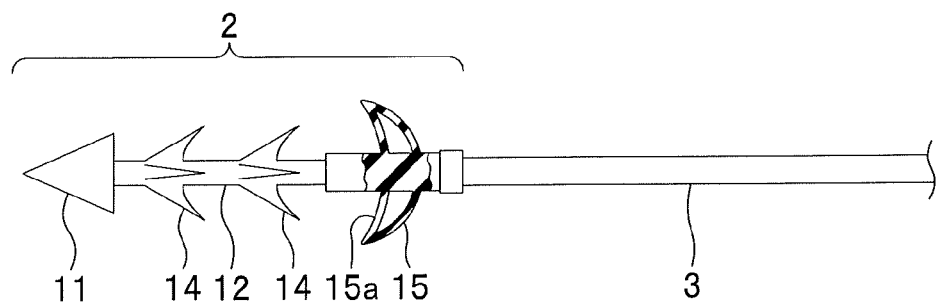
FIG. 7 is a partial sectional view showing a configuration of a tissue sampling unit according to a second variation of the first embodiment.
Figure 8:
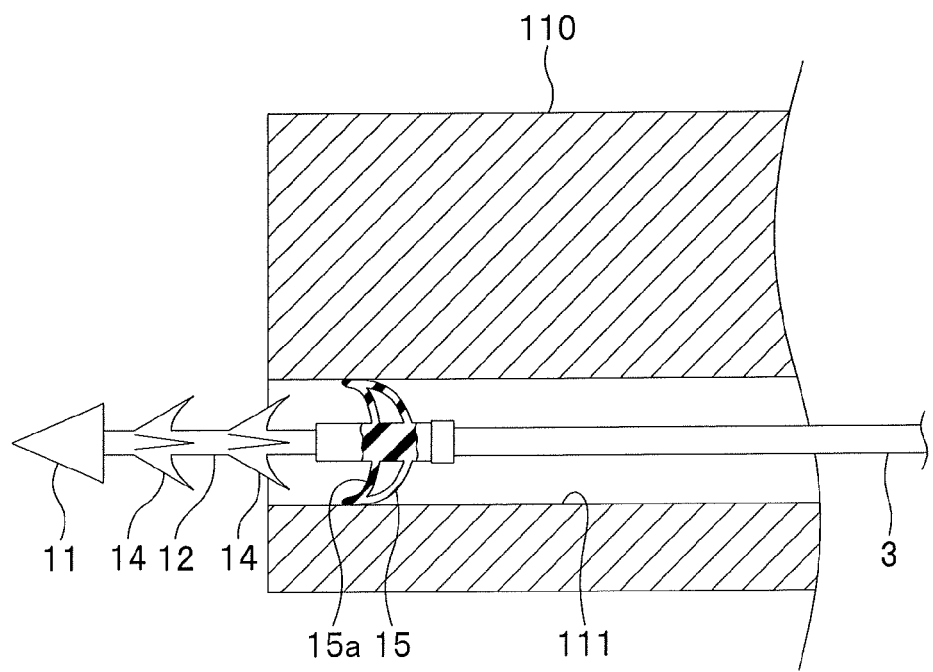
FIG. 8 is a diagram showing how the biopsy tissue sampling treatment instrument in FIG. 7 is passed through a channel of an endoscope, according to the second variation of the first embodiment.

A biopsy tissue sampling treatment instrument according to the present invention will be described with reference to the drawings. FIGS. 1 to 8 concern a first embodiment of the present invention, where FIG. 1 is a diagram showing a configuration of a biopsy tissue sampling treatment instrument, FIG. 2 is a perspective view showing a configuration of a tissue sampling unit, FIG. 3 is a sectional view showing the configuration of the tissue sampling unit, FIG. 4 is a sectional view showing how living tissue is punctured by the tissue sampling unit, FIG. 5 is a sectional view showing how the tissue sampling unit is pulled out of the living tissue and tissue fragments scraped off are held by the tissue sampling unit, FIG. 6 is a sectional view showing a configuration of a tissue sampling unit according to a first variation, FIG. 7 is a partial sectional view showing a configuration of a tissue sampling unit according to a second variation, and FIG. 8 is a diagram showing how the biopsy tissue sampling treatment instrument in FIG. 7 is passed through a channel of an endoscope.

As shown in FIG. 1, the biopsy tissue sampling treatment instrument 1 according to the present embodiment includes a tissue sampling unit 2 serving as a distal end portion, a flexible wire unit 3 serving as an insertion portion, and a grasping portion 4 serving as an operation portion, which are installed consecutively in this order starting from a distal end.

The tissue sampling unit 2 is made of a metal material or a rigid material. As shown in FIGS. 1 and 2, the tissue sampling unit 2 includes a puncturing portion 11 conical in shape and provided at a distal end, a stem portion 12 which is a rod body with a circular cross section, and a stopper portion 13. Multiple blades 14 are formed around the stem portion 12, making up a protruding portion which protrudes, in two rows in this example, in a longitudinal direction. The blades 14 are formed integrally with the stem portion 12, for example, by cutting and bristling outer circumferential part of the stem portion 12.

The flexible wire unit 3 is fixedly fitted at a distal end to the stopper portion 13 of the tissue sampling unit 2 and is made of a metal wire with predetermined flexibility, where the metal wire is set to a predetermined length according to the channel of the endoscope (not shown). The grasping portion 4 is fixedly fitted to a proximal end of the flexible wire unit 3. In a proximal end portion, the grasping portion 4 is provided with a finger grip ring portions 5 (see FIG. 1).

The puncturing portion 11 of the tissue sampling unit 2 has a pointed shape on a distal side. On a proximal side, the puncturing portion 11 has a conical surface 11a which is formed at a predetermined acute angle of 90° or less with respect to a long axis of the stem portion 12 as shown in FIG. 3. Also, each of the blades 14 has a tissue holding surface 14a formed at a predetermined acute angle of 90° or less with respect to the longitudinal axis of the stem portion 12. The stopper portion 13 has a stopper surface 13a formed at approximately 90° with respect to the long axis of the stem portion 12.

That is, the conical surface 11a of the puncturing portion 11 and the tissue holding surfaces 14a of the multiple blades 14 face the stopper surface 13a of the stopper portion 13 at predetermined angles.

The stopper portion 13 has an approximately hemispherical shape. Also, around the long axis of the stem portion 12, the stopper portion 13 has an outer circumferential shape larger than outer circumferential part of the puncturing portion 11 and amounts of protrusion of the multiple blades 14. That is, the stopper portion 13 is configured such that diameter d of the stopper surface 13a will be larger in a dimension around the longitudinal axis of the stem portion 12 than the puncturing portion 11 and the multiple blades 14.

Consequently, the tissue sampling unit 2 is configured such that the puncturing portion 11 and the multiple blades 14 are kept clear of an inner circumferential surface of the channel during passage through the channel (not shown) of the endoscope. The inner circumferential surface of the channel may be damaged by contact with the multiple blades 14 in particular. Thus, the tissue sampling unit 2 is configured to prevent the multiple blades 14 from contacting the inner circumferential surface of the channel by increasing outside diameter of the stopper portion 13 and thereby prevent damage to the inner circumferential surface of the channel. Also, the stopper portion 13, which has a spherical surface on a rear side, makes it easy to retract the tissue sampling unit 2 into the channel (not shown) of the endoscope and provides the advantage of further preventing damage to the inner circumferential surface of the channel.

The biopsy tissue sampling treatment instrument 1 according to the present embodiment with the above configuration is introduced, for example, into a bronchus which is a lumen in the body via the endoscope (not shown). Then, a predetermined site of the bronchus is punctured by the tissue sampling unit 2 of the biopsy tissue sampling treatment instrument 1 to extract part of a living body from the patient and conduct histopathological examination such as electron microscopy or chemical testing of the extracted tissue.

In so doing, the tissue sampling unit 2 is stuck into bronchial tissue 100, including the puncturing portion 11 and the entire stem portion 12 provided with the multiple blades 14, as shown in FIG. 4. Also, the stopper surface 13a of the stopper portion 13 abuts against an inner wall of the bronchus which is a lumen in the body to restrain the tissue sampling unit 2 from penetrating deeply into the tissue 100. In other words, the tissue sampling unit 2 is configured such that the stopper surface 13a of the stopper portion 13 will abut against an inner wall (a surface of the tissue 100) of the bronchus which is a lumen in the body, defining puncture depth in the tissue 100 to restrain the puncturing portion 11 and the stem portion 12 provided with the multiple blades 14 from penetrating too deeply into the tissue 100 to be punctured.

Subsequently, the biopsy tissue sampling treatment instrument 1 is hauled in and the tissue sampling unit 2 is pulled out of the punctured bronchial tissue 100 as shown in FIG. 5. Tissue fragments 101 of the punctured tissue 100 are held to the tissue sampling unit 2 by adhering to around the stem portion 12.

That is, the tissue 100 in the part punctured by the tissue sampling unit 2 is scraped by being caught by the conical surface 11a formed at a rear end of the puncturing portion 11 and the tissue holding surfaces 14a of the multiple blades 14 formed around the stem portion 12. Then, the tissue fragments 101 scraped off the tissue 100 are collected by being held around the stem portion 12.

The tissue fragments 101 are held around the stem portion 12 by being pinched between the conical surface 11a of the puncturing portion 11 and the stopper surface 13a of the stopper portion 13 as well as between the tissue holding surfaces 14a of the multiple blades 14 and the stopper surface 13a of the stopper portion 13.

Thus, the biopsy tissue sampling treatment instrument 1 according to the present embodiment can extract tissue fragments 101 easily and in sufficient quantities from the bronchial tissue 100 using the tissue sampling unit 2 of a simple configuration. That is, since the conical surface 11a of the puncturing portion 11 and the tissue holding surfaces 14a of the multiple blades 14 are placed so as to face the stopper surface 13a of the stopper portion 13, the tissue sampling unit 2 according to the present embodiment can scrape a sufficient quantity of tissue fragments 101 when pulled out of the tissue 100, and provides increased holding capacity by pinching the scraped tissue fragments 101.

Also, since the tissue sampling unit 2 is provided with the stopper portion 13, it is possible to define predetermined depth in the tissue 100 to be punctured. That is, with the biopsy tissue sampling treatment instrument 1, even when different locations of a lumen in the body, i.e., the bronchus in this case, are punctured by the tissue sampling unit 2, puncture depth of the tissue sampling unit 2 in the tissue 100 is kept substantially constant, making it possible to scrape tissue fragments 101 from the tissue 100 at a stable depth.

Thus, the biopsy tissue sampling treatment instrument 1 according to the present embodiment increases holding capacity for the living tissue to be extracted, allows living tissue to be extracted in sufficient sampling quantities, and makes it easy to take samples of living tissue at an intended depth in tissue.

Incidentally, as shown in FIG. 6, the multiple blades 14 protruding from around the stem portion 12 may be arranged in a staggered manner along the longitudinal axis of the stem portion 12.

Furthermore, as shown in FIGS. 7 and 8, a stopper portion 15 may be formed of, for example, an elastic material. The stopper portion 15 is made hollow so that a front portion will provide a stopper surface 15a, and diameter around the longitudinal axis of the tissue sampling unit 2 is configured to be variable.

Outside diameter of the stopper portion 15 is set to be larger than inside diameter of the channel 111 of the endoscope 110. Thus, the biopsy tissue sampling treatment instrument 1 is configured such that during passage through the channel 111 of the endoscope 110, the stopper portion 15 is deformed and placed in close contact with the inner circumferential surface of the channel 111 as shown in FIG. 8. That is, if the stopper portion 15 is configured to be elastically deformable, the stopper portion 15 does not need to have a diameter size which will fit in bore size of the channel 111 of the endoscope 110.

This makes it possible to increase the outside diameter around the longitudinal axis of the tissue sampling unit 2 and thereby increase the area of the stopper surface 15a which abuts the inner wall of the bronchus which is a lumen in the body. Consequently, the biopsy tissue sampling treatment instrument 1 can reliably define predetermined depth in the tissue 100 to be punctured, ensuring that the stopper surface 15a will abut the inner wall of the bronchus and thereby restraining the tissue sampling unit 2 from penetrating too deeply into the tissue 100.

The stopper portion 15 may be made of a balloon which can inflate and deflate so that the diameter around the longitudinal axis will be variable.

Second Embodiment

Figure 9:
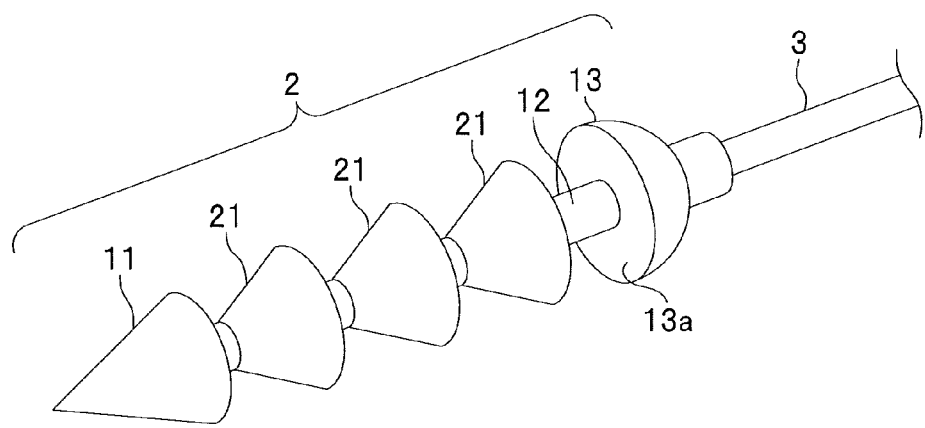
FIG. 9 is a perspective view showing a configuration of a tissue sampling unit according to a second embodiment.
Figure 10:
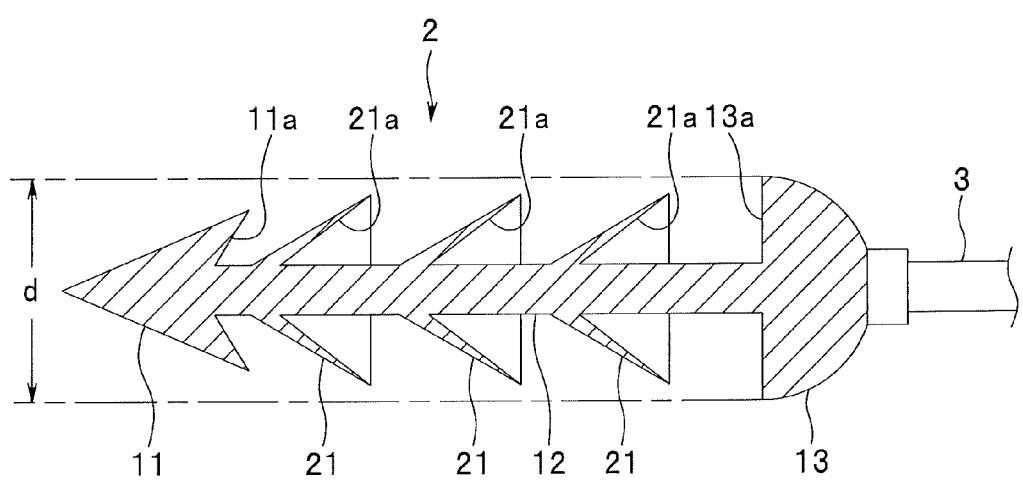
FIG. 10 is a sectional view showing the configuration of the tissue sampling unit according to the second embodiment.
Figure 11:
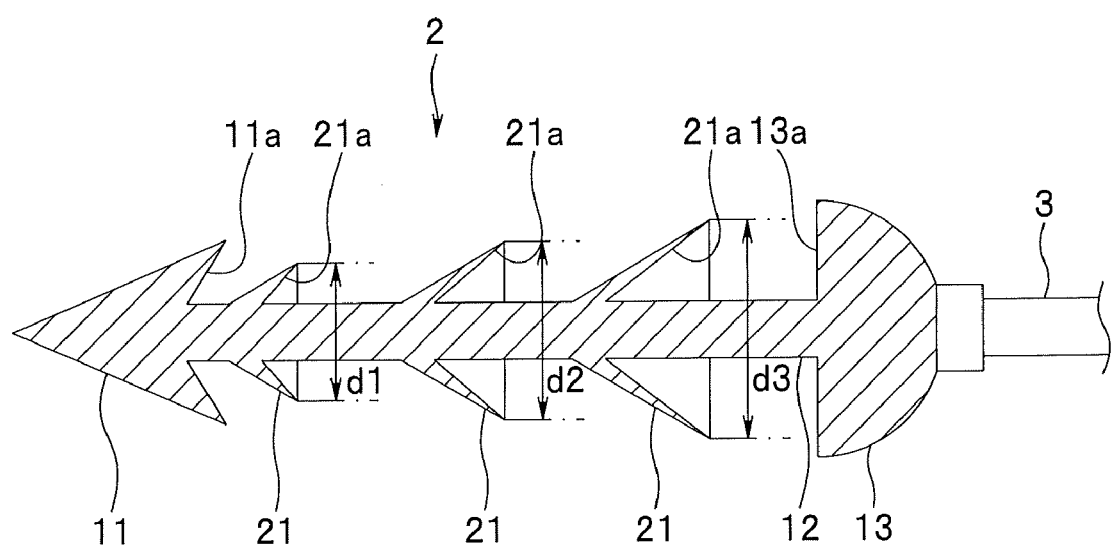
FIG. 11 is a sectional view showing a configuration of a tissue sampling unit according to a variation of the second embodiment.

Next, a second embodiment of a biopsy tissue sampling treatment instrument according to the present invention will be described below with reference to FIGS. 9 to 11. FIGS. 9 to 11 concern the second embodiment of the present invention, where FIG. 9 is a perspective view showing a configuration of the tissue sampling unit, FIG. 10 is a sectional view showing the configuration of the tissue sampling unit, and FIG. 11 is a sectional view showing a configuration of a tissue sampling unit according to a variation. In the following description, the same components as those of the biopsy tissue sampling treatment instrument according to the first embodiment are denoted by the same reference numerals as the corresponding components in the first embodiment, and description of the components and their operation and advantages will be omitted.

The biopsy tissue sampling treatment instrument 1 according to the present embodiment has thin conical blades 21 disposed at predetermined intervals around the stem portion 12, in three rows in this case, as shown in FIGS. 9 and 10 instead of the multiple blades 14 arranged around the stem portion 12 of the tissue sampling unit 2 described in the first embodiment.

Each of the blades 21 has a tissue holding surface 21a which is a conical surface formed on a proximal side at a predetermined acute angle of 90° or less with respect to the long axis of the stem portion 12. The tissue holding surfaces 21a face the stopper surface 13a of the stopper portion 13 at a predetermined angle.

As in the case of the first embodiment, the stopper surface 13a of the stopper portion 13 has a larger outer circumferential shape around the long axis of the stem portion 12 than the outer circumferential part of the puncturing portion 11 and the outer circumferential part of the multiple blades 21, and the diameter d of the stopper surface 13a is set such that the dimension around the longitudinal axis of the stem portion 12 will be larger than those of the puncturing portion 11 and the multiple blades 21.

The biopsy tissue sampling treatment instrument 1 according to the present embodiment with the above configuration has advantages similar to those of the first embodiment. Furthermore, the tissue holding surface 21a of each blade 21 of the tissue sampling unit 2 has a larger area, which accordingly ensures that larger quantities of tissue fragments 101 will be scraped and extracted from the tissue 100 and increases holding capacity for holding the tissue fragments 101 around the stem portion 12.

Incidentally, as shown in FIG. 11, the blades 21 disposed on the stem portion 12 may be set to increase gradually in maximum outside diameter from the distal end rearward. That is, a maximum outside diameter d1 of the blade 21 disposed at the most distal end, a maximum outside diameter d2 of the blade 21 disposed in the middle, and a maximum outside diameter d3 of the blade 21 disposed at the most proximal end may be set to satisfy the relationship d1<d2<d3.

This configuration improves puncture performance of the tissue sampling unit 2 of the biopsy tissue sampling treatment instrument 1 according to the present embodiment in puncturing the tissue 100.

Third Embodiment

Figure 12:
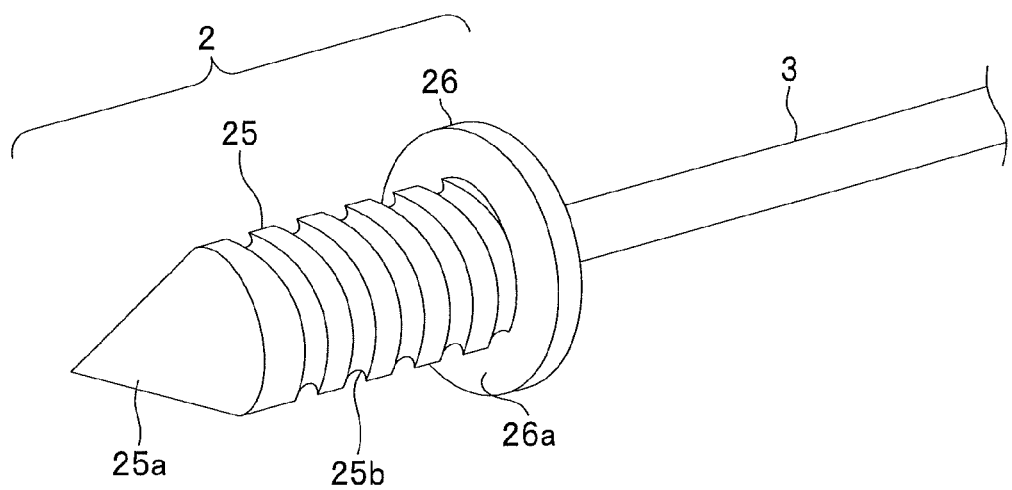
FIG. 12 is a perspective view showing a configuration of a tissue sampling unit according to a third embodiment.

Next, a third embodiment of a biopsy tissue sampling treatment instrument according to the present invention will be described below with reference to FIG. 12. FIG. 12 is a perspective view showing a configuration of the tissue sampling unit according to the third embodiment. Again, in the following description, the same components as those of the biopsy tissue sampling treatment instrument according to the first embodiment are denoted by the same reference numerals as the corresponding components in the first embodiment, and description of the components and their operation and advantages will be omitted.

A tissue sampling unit 2 of the biopsy tissue sampling treatment instrument 1 according to the present embodiment shown in FIG. 12 includes a tissue holding body 25 with a spiral structure provided in outer circumferential part, and a stopper portion 26 shaped as an outward flange and disposed in a proximal end portion of the tissue holding body 25.

The tissue holding body 25 has a sharp-edged portion 25a whose distal end is formed into a conical shape. On the proximal side of the sharp-edged portion 25a, a spiral groove 25b is formed on a cylindrical outer circumferential surface. Also, a front portion of the stopper portion 26 provides a stopper surface 26a, projecting more outwardly in a vertical direction than outer circumferential part of the tissue holding body 25.

When the tissue sampling unit 2 configured as described above is stuck into the tissue 100, for example, through the inner wall of the bronchus, the stopper surface 26a of the stopper portion 26 abuts the inner wall of the bronchus, restraining the tissue holding body 25 from penetrating too deeply into the tissue 100, as in the case of the first embodiment. With the tissue holding body 25, the punctured tissue 100 getting into the spiral groove 25b is caught by the spiral groove 25b and when the tissue holding body 25 is pulled out of the tissue 100, tissue fragments 101 are scraped off and extracted by being held in the spiral groove 25b.

Thus, the tissue sampling unit 2 of the biopsy tissue sampling treatment instrument 1 according to the present embodiment provide advantages similar to those of the first embodiment except that tissue fragments 101 can be extracted in smaller quantities.

Fourth Embodiment

Figure 13:
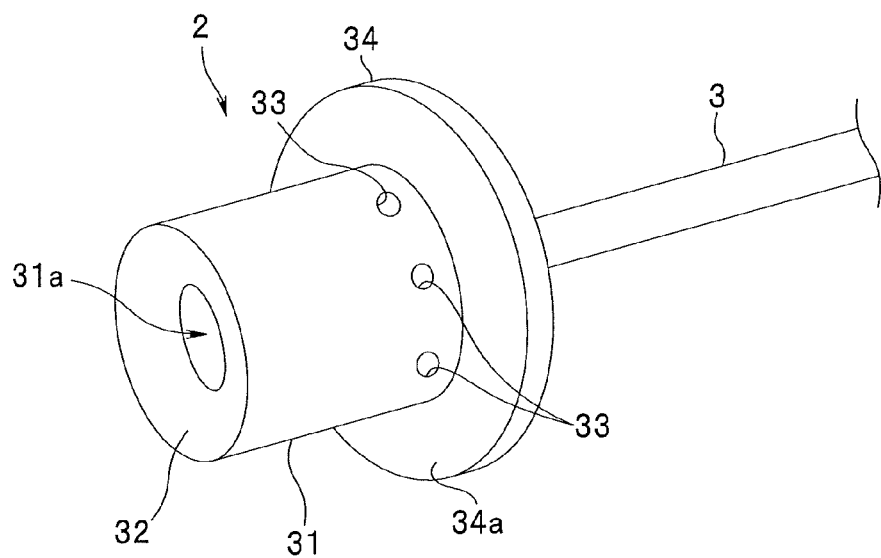
FIG. 13 is a perspective view showing a configuration of a tissue sampling unit according to a fourth embodiment.
Figure 14:
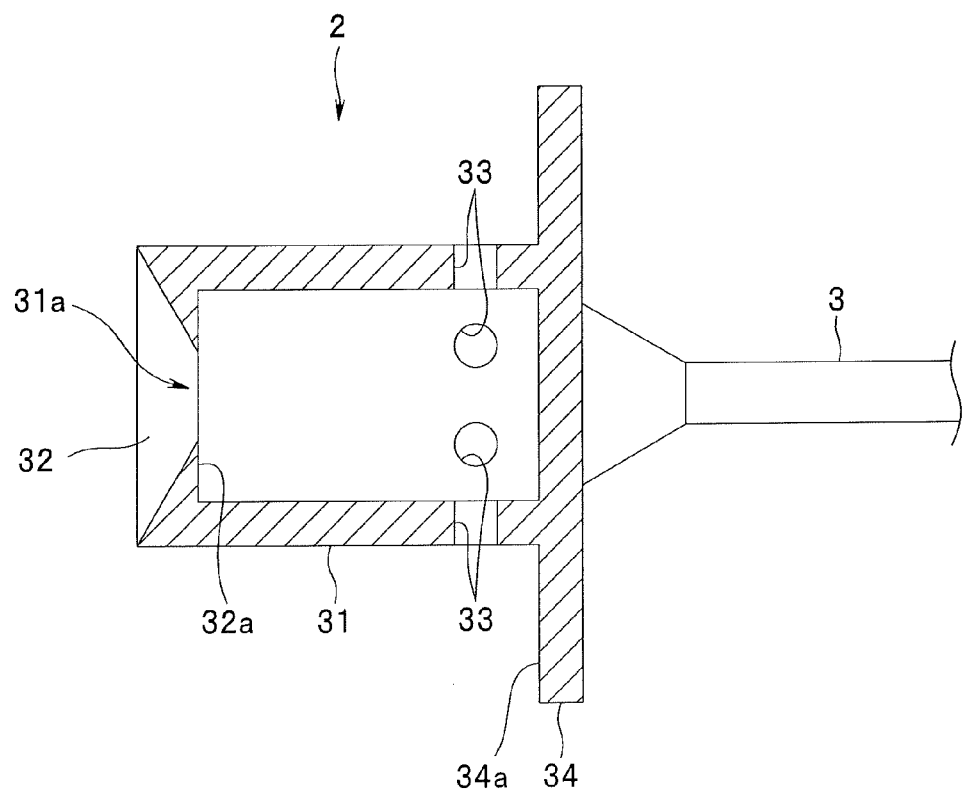
FIG. 14 is a sectional view showing the configuration of the tissue sampling unit according to the fourth embodiment.
Figure 15:
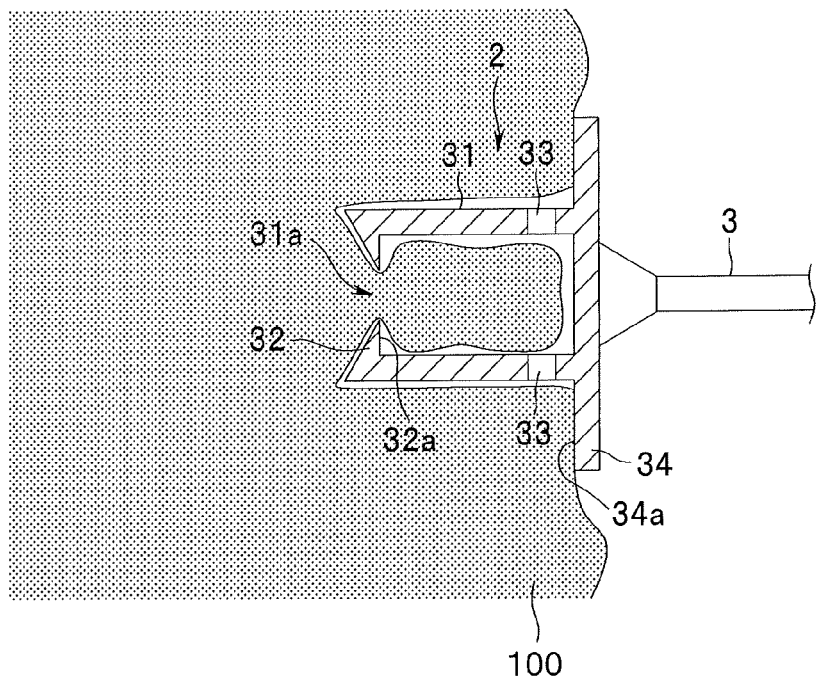
FIG. 15 is a sectional view showing how living tissue is punctured by the tissue sampling unit, according to the fourth embodiment.
Figure 16:
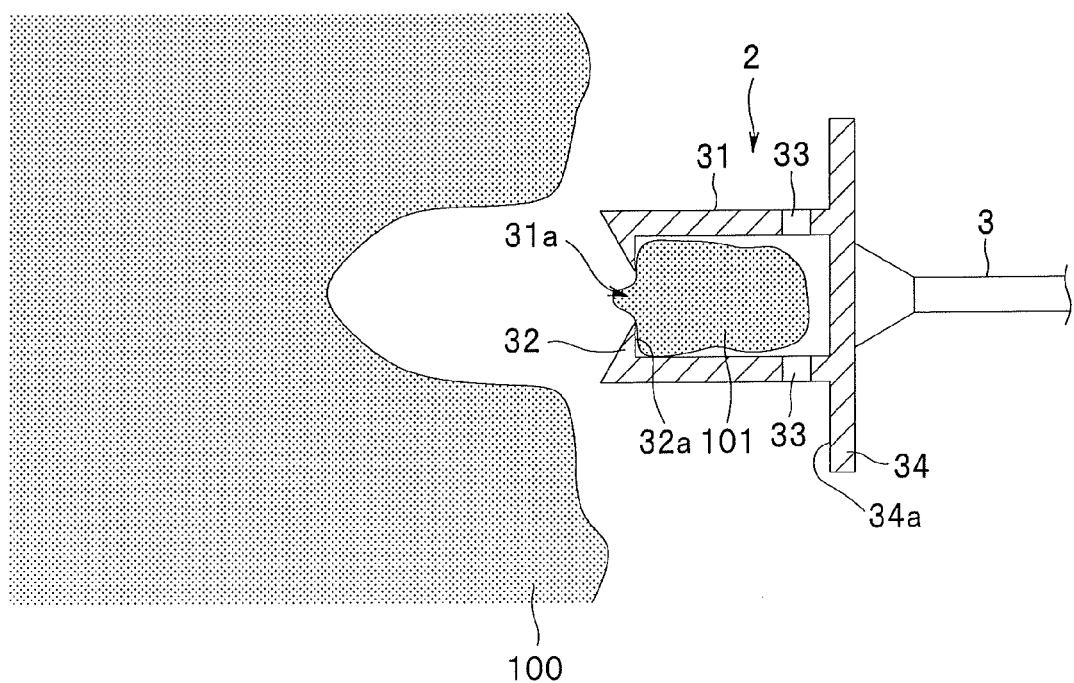
FIG. 16 is a sectional view showing how the tissue sampling unit is pulled out of the living tissue and tissue fragments scraped off are held by the tissue sampling unit, according to the fourth embodiment.

Next, a fourth embodiment of a biopsy tissue sampling treatment instrument according to the present invention will be described below with reference to FIGS. 13 to 16. FIGS. 13 to 16 concern the fourth embodiment of the present invention, where FIG. 13 is a perspective view showing a configuration of a tissue sampling unit, FIG. 14 is a sectional view showing the configuration of the tissue sampling unit, FIG. 15 is a sectional view showing how living tissue is punctured by the tissue sampling unit, and FIG. 16 is a sectional view showing how the tissue sampling unit is pulled out of the living tissue and tissue fragments scraped off are held by the tissue sampling unit. Again, in the following description, the same components as those of the biopsy tissue sampling treatment instrument according to the first embodiment are denoted by the same reference numerals as the corresponding components in the first embodiment, and description of the components and their operation and advantages will be omitted.

As shown in FIGS. 13 and 14, the tissue sampling unit 2 of the biopsy tissue sampling treatment instrument 1 according to the present embodiment includes a tissue holding body 31 which is approximately tubular in shape and whose proximal end is closed, and a stopper portion 34 shaped as an outward flange and disposed in a proximal end portion of the tissue holding body 31.

The tissue holding body 31 has a blade 32 formed along a circumference of a distal opening 31a by extending in a radially inward direction as an inward flange. Also, the tissue holding body 31 has a row of multiple air vent hole portions 33 formed along an outer circumference on a proximal side. A front face of the blade 32 is tapered toward the proximal side, and a proximal end face in the tissue holding body 31 forms a tissue holding surface 32a along a direction of extension.

A front portion of the stopper portion 34 provides a stopper surface 34a, projecting more outwardly in the vertical direction than outer circumferential part of the tissue holding body 31. The stopper surface 34a is parallel to the tissue holding surface 32a of the blade 32.

As the tissue sampling unit 2 of the biopsy tissue sampling treatment instrument 1 is configured as described above, when the entire tissue holding body 31 is stuck into the tissue 100 of the bronchus, part of the tissue 100 gets into the tissue holding body 31 through the distal opening 31a as shown in FIG. 15. Since air is released from the tissue holding body 31 through the multiple hole portions 33, part of the tissue 100 gets into the tissue holding body 31 smoothly.

Then, with the stopper surface 34a of the stopper portion 34 abutting the inner wall of the bronchus, the tissue sampling unit 2 is restrained from penetrating deep into the tissue 100.

In this way, again in the present embodiment, the tissue sampling unit 2 is configured such that the stopper surface 34a of the stopper portion 34 will abut against the inner wall of the bronchus, defining puncture depth in the tissue 100 to restrain the tissue holding body 31 on the distal side from penetrating too deeply into the tissue 100 to be punctured.

Subsequently, the biopsy tissue sampling treatment instrument 1 is hauled in and the tissue sampling unit 2 is pulled out of the punctured bronchial tissue 100 as shown in FIG. 16. In so doing, part of the punctured tissue 100 is scraped off by being caught by the blade 32 and is held as tissue fragments 101 in the tissue holding body 31 of the tissue sampling unit 2. That is, the tissue fragments 101 scraped off the tissue 100 are collected by being held in the tissue holding body 31.

The tissue fragments 101 are placed in abutment with the tissue holding surface 32a of the blade 32 and thereby kept from falling off. Consequently, being held securely by the tissue holding surface 32a and an inner surface of the tissue holding body 31 approximately cylindrical in shape, the tissue fragments 101 are housed in the tissue holding body 31.

The biopsy tissue sampling treatment instrument 1 according to the present embodiment with the above configuration has advantages similar to those of the first embodiment. Furthermore, large quantities of tissue fragments 101 can be scraped off the tissue 100 depending on a volume of the tissue holding body 31, and the tissue fragments 101 housed in the tissue holding body 31 can be held and collected reliably.

Fifth Embodiment

Figure 17:
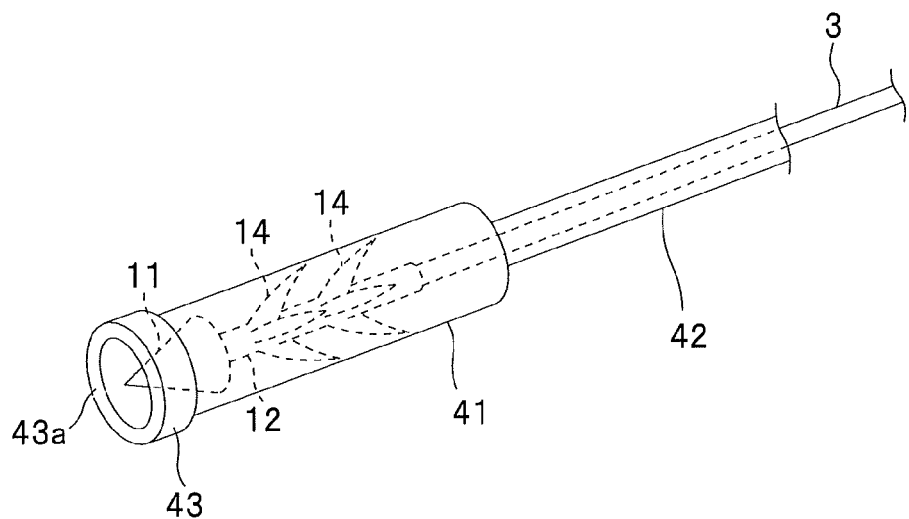
FIG. 17 is a perspective view showing a configuration of a protector which protects a tissue sampling unit according to a fifth embodiment.
Figure 18:
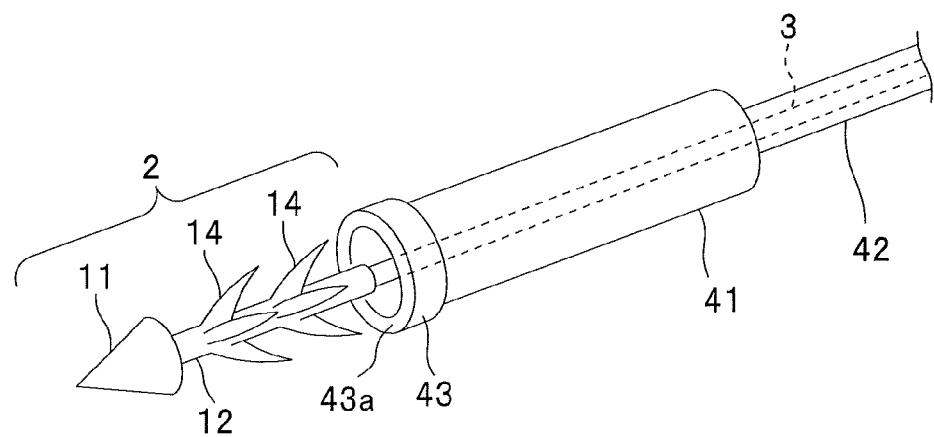
FIG. 18 is a perspective view showing how the tissue sampling unit is extended from the protector, according to the fifth embodiment.

Next, a fifth embodiment of a biopsy tissue sampling treatment instrument according to the present invention will be described below with reference to FIGS. 17 and 18. FIGS. 17 and 18 concern the fifth embodiment of the present invention, where FIG. 17 is a perspective view showing a configuration of a protector which protects a tissue sampling unit and FIG. 18 is a perspective view showing how the tissue sampling unit is extended from the protector. Again, in the following description, the same components as those of the biopsy tissue sampling treatment instrument according to the first embodiment are denoted by the same reference numerals as the corresponding components in the first embodiment, and description of the components and their operation and advantages will be omitted.

As shown in FIGS. 17 and 18, the biopsy tissue sampling treatment instrument 1 according to the present embodiment includes a cover body 41 which is an approximately cylindrical protecting portion configured to cover the tissue sampling unit 2.

An operation tube 42 is installed consecutively with a proximal end of the cover body 41 by being set to a length dimension shorter than the flexible wire unit 3 and fitted over the flexible wire unit 3 in such a way as to be able to move forward and backward. That is, as the operation tube 42 or the flexible wire unit 3 is hand-controlled, the cover body 41 and the tissue sampling unit 2 are caused to slide relative to each other, switching the tissue sampling unit 2 between two states: a state of being housed in the cover body 41 and a state of being exposed from the cover body 41.

Also, an outwardly flanged stopper portion 43 is disposed around a distal opening of the cover body 41. Consequently, the tissue sampling unit 2 according to the present embodiment does not include the stopper portion 13 described in the first embodiment.

That is, the stopper portion 43 of the cover body 41 allows the puncture depth of the tissue sampling unit 2 to be adjusted based on an amount of extension by which the tissue sampling unit 2 is extended from the distal opening of the cover body 41. In other words, since length of the tissue sampling unit 2 to be extended from the cover body 41 can be changed freely by hand-controlling the operation tube 42 or the flexible wire unit 3, in addition to the advantages of the first embodiment, the present embodiment provides the advantage that the stopper portion 43 of the cover body 41 can freely define the puncture depth of the tissue sampling unit 2 in the tissue 100 as a stopper surface 43a abuts, for example, against the inner wall of the bronchus.

Furthermore, when passed through, or pulled out of, the channel (not shown) of the endoscope, the biopsy tissue sampling treatment instrument 1 according to the present embodiment covers the tissue sampling unit 2 with the cover body 41 to prevent the inside of the channel from being damaged by the multiple blades 14.

Sixth Embodiment

Figure 19:
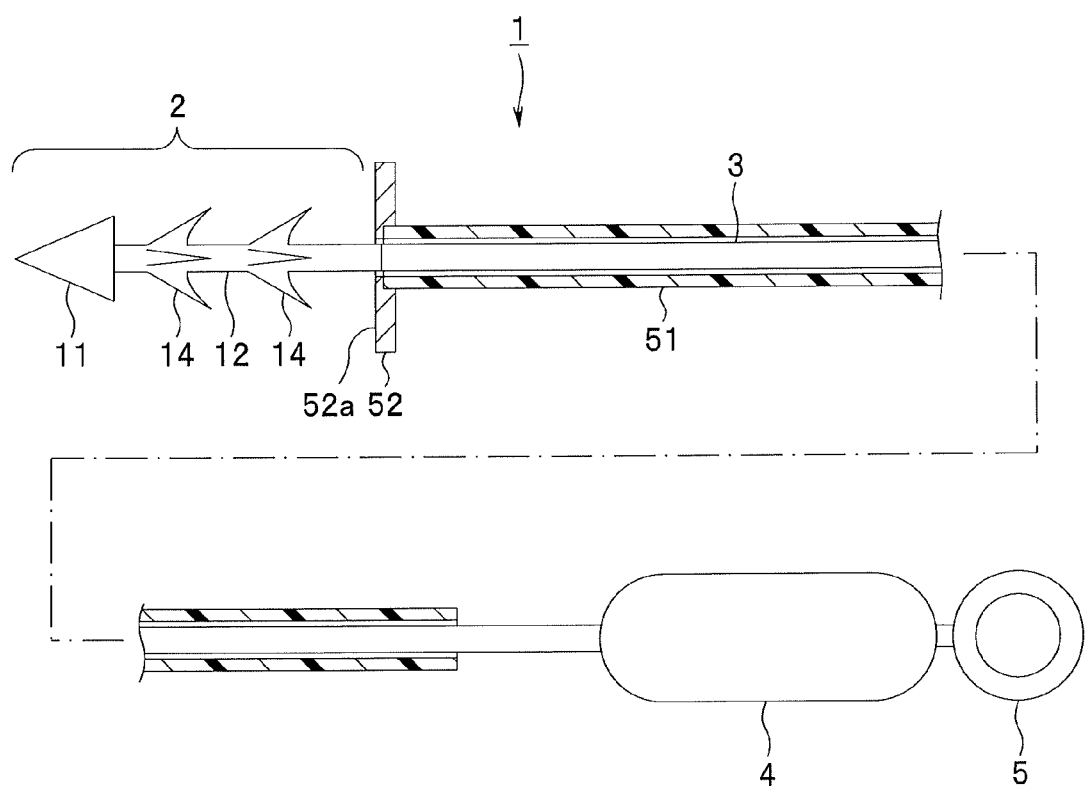
FIG. 19 is a partial sectional view showing a configuration of a biopsy tissue sampling treatment instrument equipped with an overtube having a stopper portion according to a sixth embodiment.
Figure 20:
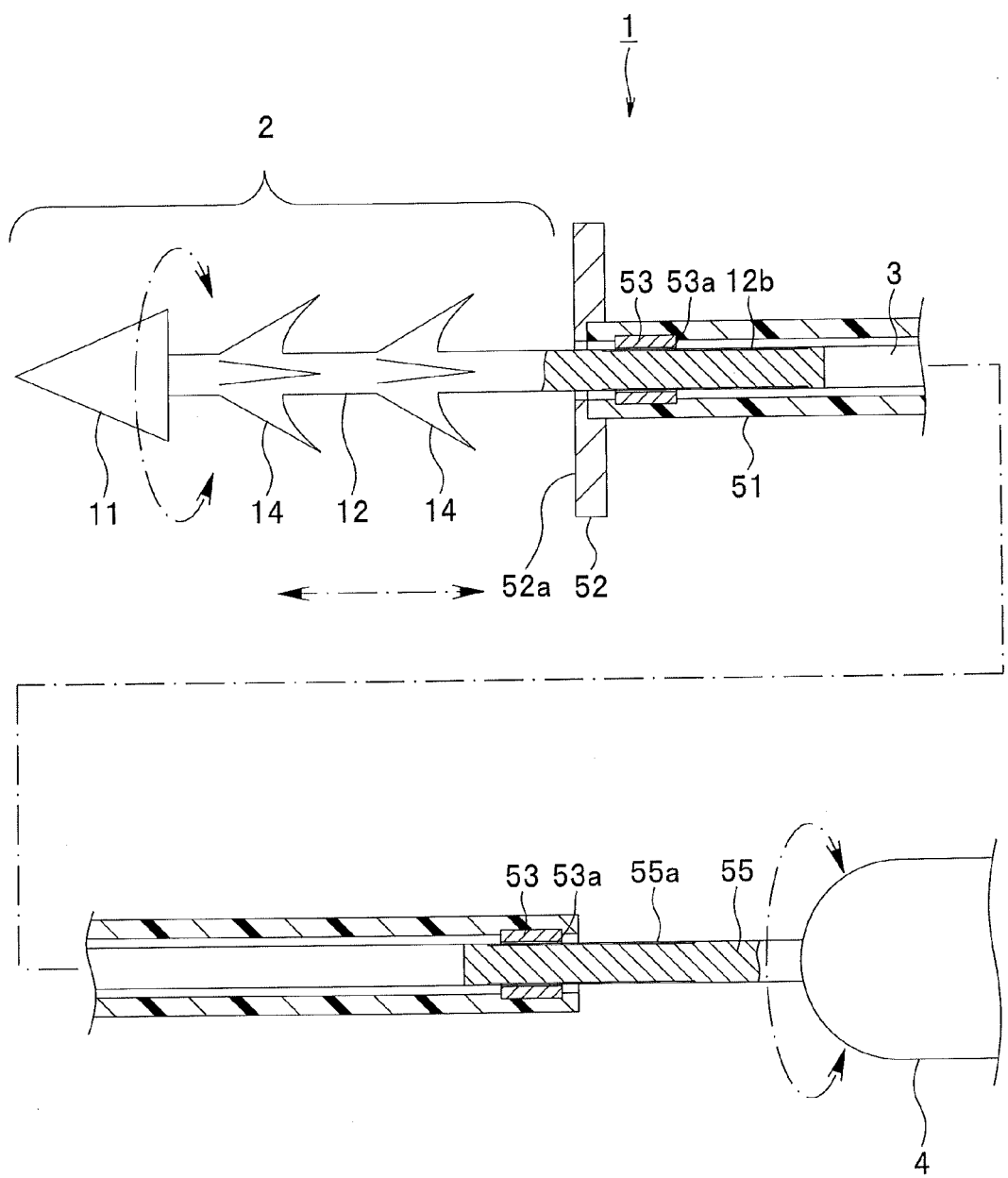
FIG. 20 is a partial sectional view showing a configuration of a biopsy tissue sampling treatment instrument equipped with an overtube having a stopper portion according to a first variation of the sixth embodiment.
Figure 21:
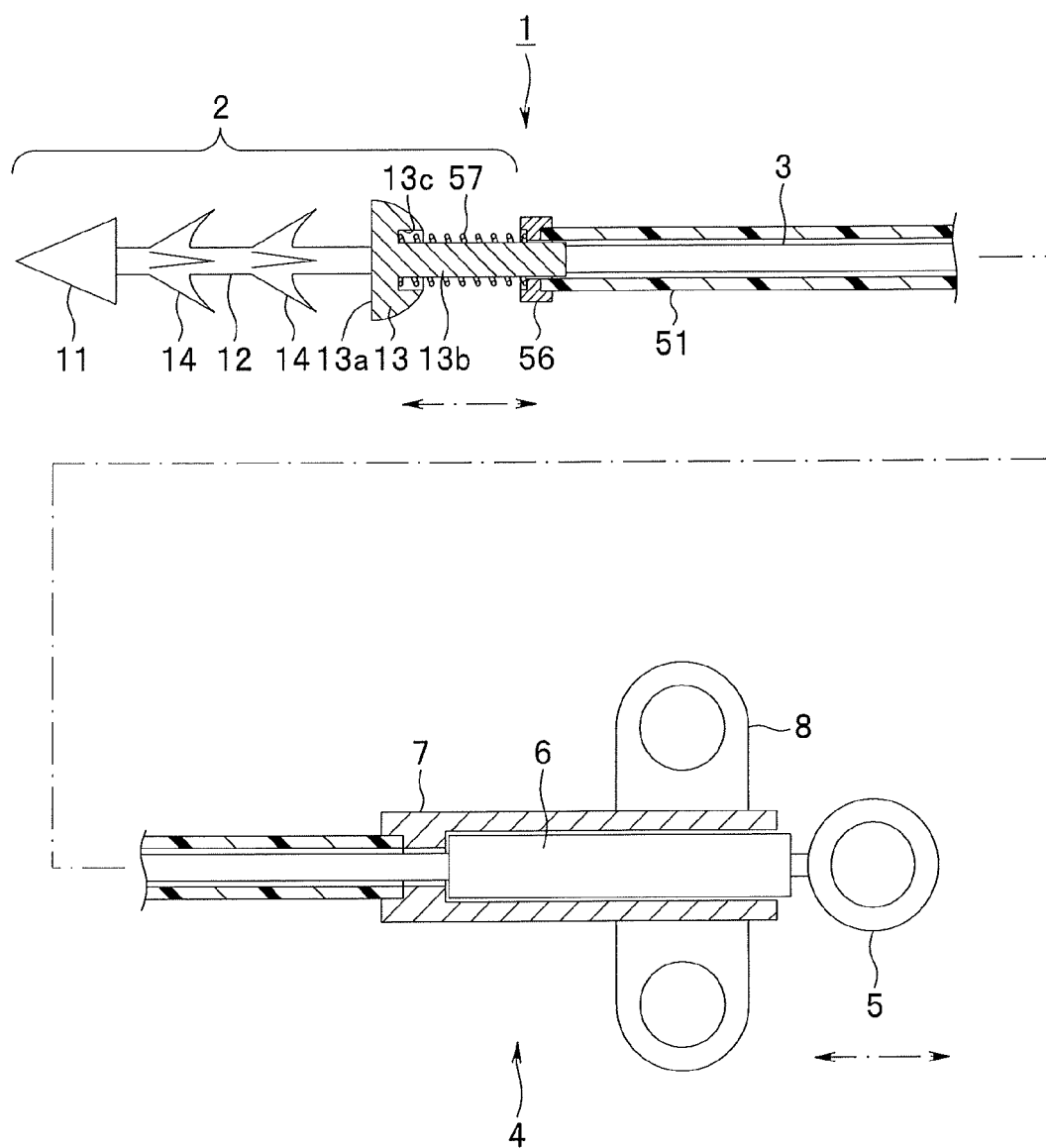
FIG. 21 is a partial sectional view showing a configuration of a biopsy tissue sampling treatment instrument equipped with an overtube according to a second variation of the sixth embodiment.
Figure 22:
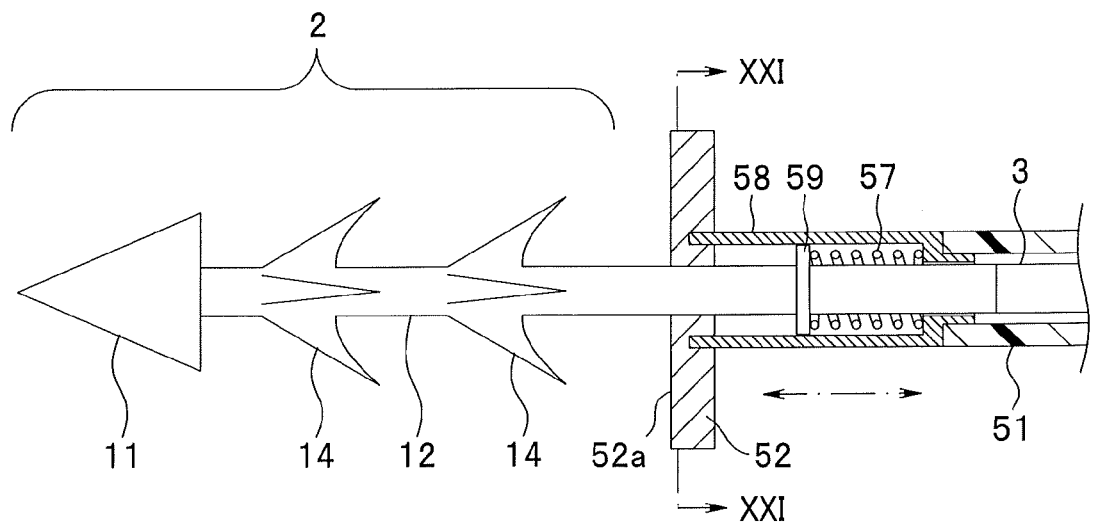
FIG. 22 is a partial sectional view showing a configuration of a biopsy tissue sampling treatment instrument equipped with an overtube having a stopper portion according to a third variation of the sixth embodiment.
Figure 23:
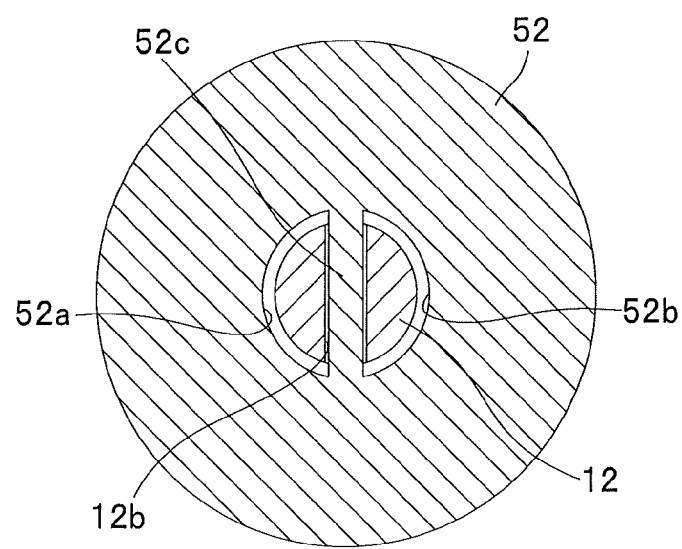
FIG. 23 is a sectional view taken along line XXIII-XXIII in FIG. 22 according to the third variation of the sixth embodiment.

Next, a sixth embodiment of a biopsy tissue sampling treatment instrument according to the present invention will be described below with reference to FIGS. 19 to 23. FIGS. 19 to 23 concern the sixth embodiment of the present invention, where FIG. 19 is a partial sectional view showing a configuration of a biopsy tissue sampling treatment instrument equipped with an overtube having a stopper portion, FIG. 20 is a partial sectional view showing a configuration of a biopsy tissue sampling treatment instrument equipped with an overtube having a stopper portion according to a first variation, FIG. 21 is a partial sectional view showing a configuration of a biopsy tissue sampling treatment instrument equipped with an overtube according to a second variation, FIG. 22 is a partial sectional view showing a configuration of a biopsy tissue sampling treatment instrument equipped with an overtube having a stopper portion according to a third variation, and FIG. 23 is a sectional view taken along line XXIII-XXIII in FIG. 22. Again, in the following description, the same components as those of the biopsy tissue sampling treatment instrument according to the first embodiment are denoted by the same reference numerals as the corresponding components in the first embodiment, and description of the components and their operation and advantages will be omitted.

As shown in FIG. 19, the biopsy tissue sampling treatment instrument 1 according to the present embodiment includes an overtube 51 which is a flexible sheath body configured to pass the flexible wire unit 3 therethrough. A stopper portion 52 made of hard metal plate or the like is provided at a distal end of the overtube 51. A front portion of the stopper portion 52 provides a stopper surface 52a, projecting more outwardly in the vertical direction than outer circumferential part of the overtube 51.

The overtube 51 is able to move forward and backward along the flexible wire unit 3 by being hand-controlled by the user. This allows distance between the tissue sampling unit 2 and the stopper portion 52 to be varied.

Thus, in addition to the advantages of the first embodiment, the biopsy tissue sampling treatment instrument 1 according to the present embodiment has the advantage of allowing the user to change an amount of puncture depth of the tissue sampling unit 2 in the tissue 100 as desired by adjusting relative distance between the stopper portion 52 of the overtube 51 and the tissue sampling unit 2.

(First Variation)

As shown in FIG. 20, the biopsy tissue sampling treatment instrument 1 according to the present variation has a tubular threaded portion 53 provided in inner circumferential part of both distal part and proximal part of the overtube 51, where a thread groove 53a is cut in an inner circumferential surface of each threaded portion 53.

A thread groove 12b is formed to a predetermined length in outer circumferential part of proximal part of the stem portion 12 of the tissue sampling unit 2 to mesh with the threaded portion 53 on the distal side. On the other hand, the threaded portion 53 on the proximal side meshes with a thread groove 55a formed to a predetermined length in outer circumferential part of a rod body 55 extending from the grasping portion 4 and connected to the flexible wire unit 3.

With this configuration, by rotating the grasping portion 4 around an axis of the flexible wire unit 3, it is possible to vary and fix the relative position (separation distance) between a distal end (the puncturing portion 11) of the tissue sampling unit 2 and the stopper portion 52 of the overtube 51 through the meshing of the threaded portions 53 with the thread groove 12b in the stem portion 12 and the thread groove 55a in the rod body 55, respectively.

In this way, by adjusting and fixing the relative distance between the stopper portion 52 of the overtube 51 and the tissue sampling unit 2, the biopsy tissue sampling treatment instrument 1 according to the present variation allows a set amount of depth to be fixed when the tissue 100 is punctured by the tissue sampling unit 2.

(Second Variation)

As shown in FIG. 21, the biopsy tissue sampling treatment instrument 1 according to the present variation has a ring-shaped spring stop member 56 provided in distal part of the overtube 51.

A coil spring 57 is disposed in front of the spring stop member 56. The coil spring 57 is fitted over a shaft 13b formed integrally with the stopper portion 13 of the tissue sampling unit 2 and is disposed such that a distal end of the coil spring 57 will come into abutment in a concave portion 13c formed at a proximal end of the stopper portion 13.

The grasping portion 4 of the biopsy tissue sampling treatment instrument 1 includes a sliding body 6, a holding body 7 tubular in shape, and two finger grip portions 8 shaped like a ring, where the sliding body 6 has a ring portion 5 disposed at the proximal end and is connected with the proximal end of the flexible wire unit 3, the holding body 7 is configured to hold the sliding body 6 and is connected with the proximal end of the overtube 51, and the finger grip portions 8 are provided in outer circumferential part of the holding body 7. That is, by moving the sliding body 6 forward or backward with respect to the holding body 7, the grasping portion 4 can haul in or relax the flexible wire unit 3.

Also, when the flexible wire unit 3 is hauled in, the tissue sampling unit 2 moves backward, compressing the coil spring 57. In this state, when the flexible wire unit 3 is relaxed, the tissue sampling unit 2 moves forward vigorously by the biasing force of the coil spring 57.

In this way, by the biasing force of the coil spring 57, the biopsy tissue sampling treatment instrument 1 according to the present variation can increase stress acting to stick the tissue sampling unit 2 into the tissue 100. Furthermore, the biopsy tissue sampling treatment instrument 1 can increase a pressing force of the stopper surface 13a of the stopper portion 13 against the tissue 100, with the tissue sampling unit 2 stuck in the tissue 100.

(Third Variation)

As shown in FIG. 22, the biopsy tissue sampling treatment instrument 1 according to the present variation has a tubular spring stop tube 58 provided at the distal end of the overtube 51 to house the coil spring 57. The spring stop tube 58 has a stopper portion 52 disposed at a distal end.

The proximal part of the stem portion 12 of the tissue sampling unit 2 is housed in the spring stop tube 58, and an outward flange 59 is provided in the middle of outer circumferential part on the proximal side to hold the distal end of the coil spring 57 in abutment. That is, in the spring stop tube 58, the coil spring 57 is fitted over the stem portion 12 in abutment with the outward flange 59 and an inner proximal end face of the spring stop tube 58.

As shown in FIG. 23, a slit 12c is formed in the center of a cross section of the stem portion 12 to allow the stem portion 12 to pass through two semispherical hole portions 52b formed in the stopper portion 52. In other words, the stopper portion 52 is configured such that a boundary portion 52c between the two hole portions 52b will be placed in the slit 12c of the stem portion 12 by passing through the slit 12c.

Consequently, the tissue sampling unit 2 is guided to travel in a straight line when moving forward or backward, with axial rotation restrained by the boundary portion 52c of the stopper portion 52.

In this way, by the biasing force of the coil spring 57, the biopsy tissue sampling treatment instrument 1 according to the present variation can increase the stress acting to stick the tissue sampling unit 2 into the tissue 100. Also, the biopsy tissue sampling treatment instrument 1 can vary the relative position (separation distance) between the distal end (puncturing portion 11) of the tissue sampling unit 2 and the stopper portion 52 of the overtube 51. Again in the present variation, the biopsy tissue sampling treatment instrument 1 can increase a pressing force of the stopper surface of the stopper portion 13 against the tissue 100, with the tissue sampling unit 2 stuck in the tissue 100.

Seventh Embodiment

Figure 24:
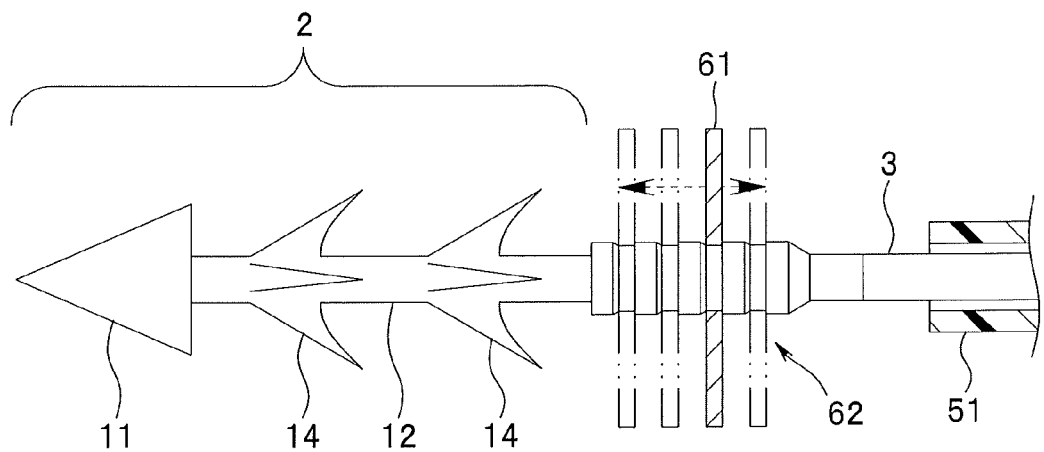
FIG. 24 is a partial sectional view showing a configuration of a biopsy tissue sampling treatment instrument capable of changing stopper portion position, according to a seventh embodiment.
Figure 25:
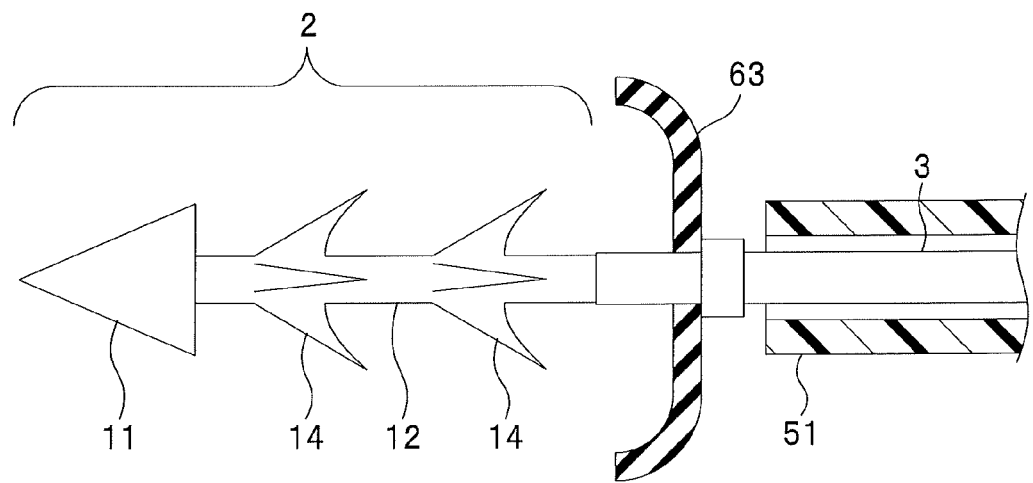
FIG. 25 is a partial sectional view showing a configuration of a biopsy tissue sampling treatment instrument equipped with a stopper portion according to a variation of the seventh embodiment.

Next, a seventh embodiment of a biopsy tissue sampling treatment instrument according to the present invention will be described below with reference to FIGS. 24 and 25. FIGS. 24 and 25 concern the seventh embodiment of the present invention, where FIG. 24 is a partial sectional view showing a configuration of a biopsy tissue sampling treatment instrument capable of changing stopper portion position and FIG. 25 is a partial sectional view showing a configuration of a biopsy tissue sampling treatment instrument equipped with a stopper portion according to a variation. Again, in the following description, the same components as those of the biopsy tissue sampling treatment instrument according to the first and sixth embodiments are denoted by the same reference numerals as the corresponding components in the first and sixth embodiments, and description of the components and their operation and advantages will be omitted.

As shown in FIG. 24, the biopsy tissue sampling treatment instrument 1 according to the present embodiment is configured to allow position of a disk-shaped stopper portion 61 disposed in the tissue sampling unit 2 to be adjusted forward and backward along an axial direction of the stem portion 12. More specifically, a restraining stepped portion 62 is provided on the stem portion 12 of the tissue sampling unit 2, where the restraining stepped portion 62 has concavo-convexities formed in proximal outer circumferential part along the axial direction. Besides, a hole portion is formed in the center of the stopper portion 61 to engage with a concave portion of the restraining stepped portion 62.

That is, the stopper portion 61 is fixed at the position of a concave portion of the restraining stepped portion 62. Also, the stopper portion 61 can climb over the convex portions of the restraining stepped portion 62 if shifted by the user with a predetermined amount of force. Consequently, the stopper portion 61 can be fixed after being adjusted forward or backward stepwise along the axial direction of the stem portion 12 within a range in which the restraining stepped portion 62 of the tissue sampling unit 2 is formed.

In this way, with the biopsy tissue sampling treatment instrument 1 according to the present embodiment, the relative position (separation distance) between the distal end (puncturing portion 11) of the tissue sampling unit 2 and the stopper portion 61 can be adjusted stepwise and fixed at a desired forward/backward position. Thus, in addition to the advantages of the first embodiment, the biopsy tissue sampling treatment instrument 1 according to the present embodiment has the advantage of allowing the user to change the amount of puncture depth of the tissue sampling unit 2 in the tissue 100 as desired by adjusting the relative distance between the stopper portion 61 and the tissue sampling unit 2.

Incidentally, as shown in FIG. 25, a stopper portion 63 disposed in the tissue sampling unit 2 may be a disk-shaped plate of an elastic material such as rubber and outer circumferential part thereof may be bent toward the distal side. With this configuration, in the biopsy tissue sampling treatment instrument 1, a resilient force of the stopper portion 63 will increase an abutting force of the stopper portion 63 against the surface of the tissue 100 and make it easy to remove the tissue sampling unit 2 from the tissue 100. Of course, the configuration of the stopper portion 63 shown in FIG. 25 is also applicable to the stopper portions according to the other embodiments.

The biopsy tissue sampling treatment instruments according to the embodiments described above increase holding capacity for the living tissue to be extracted, allow living tissue to be extracted in sufficient sampling quantities, and make it easy to take samples of living tissue at an intended depth in tissue.

What is claimed is:

1. A biopsy tissue sampling treatment instrument comprising:
   a tissue sampling unit having a predetermined length sufficient to puncture living tissue, the tissue sampling unit comprising:
      a puncturing portion formed at a distal end of the tissue sampling unit, the puncturing portion comprising:
         a protruding surface portion expanding in a rearward direction along a puncture direction of the tissue sampling unit; and
         a first tissue holding surface, provided on a rear side of the protruding surface portion, having an area large enough to hold the living tissue;
      a stopper member provided at a rear end of the tissue sampling unit so as to be separated from a first conical surface formed at a rear end of the puncturing portion by a distance corresponding to a depth at which the living tissue is extracted, the stopper member comprising an abutting portion capable of abutting against the living tissue when the tissue sampling unit punctures the living tissue;
      a stem portion connecting the puncturing portion and the stopper member; and
      a protruding portion having a conical thin blade shape and provided at the stem portion and between the first tissue holding surface and the abutting portion, the protruding portion extending in a diameter direction of the stem portion and including a second tissue holding surface which is a second conical surface formed toward the rearward direction, the second tissue holding surface having an area large enough to hold the living tissue; and
   an operating member provided on the stopper member and configured to hold the tissue sampling unit when the tissue sampling unit punctures the living tissue,
   wherein tissue fragments of the living tissue which are scraped off by the first tissue holding surface and the second tissue holding surface are collected by being held by the first tissue holding surface and the second tissue holding surface and the abutting portion.

2. The biopsy tissue sampling treatment instrument according to claim 1, wherein the first tissue holding surface protrudes toward a proximal side at an acute angle with respect to a longitudinal axis of the stem portion.

3. The biopsy tissue sampling treatment instrument according to claim 1, wherein the first tissue holding surface has a holding surface that holds tissue fragments scraped off from the punctured living tissue and faces a surface of the stopper member which abuts against a surface of the living tissue.

4. The biopsy tissue sampling treatment instrument according to claim 1, wherein the stopper member is larger in an external dimension around the longitudinal axis of the stem portion than are the puncturing portion and the first tissue holding surface, and
   the operating member includes an insertion member having flexibility and extended from a rear end of the stem portion, and the operating member is disposed at a rear end of the insertion member and holds the stem portion through the insertion member, allowing the stem portion to puncture the living tissue.

5. The biopsy tissue sampling treatment instrument according to claim 4, wherein the stopper member is configured to be variable in the external dimension around the longitudinal axis of the tissue sampling unit.

6. The biopsy tissue sampling treatment instrument according to claim 4, wherein the stopper member is disposed so as to allow a separation distance from the puncturing portion to be changed and allows a position which defines an amount of puncture depth of the tissue sampling unit and the protruding portion in the living tissue to be varied.

7. The biopsy tissue sampling treatment instrument according to claim 1, further comprising a protecting portion disposed so as to be able to move forward and backward along a longitudinal axis of the stem portion and configured to cover the tissue sampling unit and the first tissue holding surface, wherein
   the stopper member is disposed at a distal end of the protecting portion.

8. The biopsy tissue sampling treatment instrument according to claim 1, further comprising a sheath body configured to sheathe the operating member, wherein the stopper member is disposed at a distal end of the sheath body.

9. The biopsy tissue sampling treatment instrument according to claim 1, wherein tissue fragments of the living tissue scraped off by the first and second tissue holding surfaces are pinched and extracted by the first and second tissue holding surfaces and the abutting portion.

10. The biopsy tissue sampling treatment instrument according to claim 1, wherein the protruding portion is provided in plural numbers between the puncturing portion and the stopper member, each of the protruding portions having a maximum outside diameter which gradually increases from a distal end toward a proximal end.

11. A biopsy tissue sampling treatment instrument comprising:
    a tissue sampling unit having a predetermined length sufficient to puncture living tissue, the tissue sampling unit comprising:
       a puncturing portion formed at a distal end of the tissue sampling unit, the puncturing portion comprising:
          a protruding surface portion expanding in a rearward direction along a puncture direction of the tissue sampling unit; and
          a first tissue holding surface, provided on a rear side of the protruding surface portion, having an area large enough to hold the living tissue;
       a stopper member provided at a rear end of the tissue sampling unit so as to be separated from a distal end of the puncturing portion by a distance corresponding to a depth at which the living tissue is extracted, the stopper member comprising an abutting portion capable of abutting against the living tissue when the tissue sampling unit punctures the living tissue, the stopper member having a hollow structure at a rear end side of the abutting portion;
       a stem portion connecting the puncturing portion and the stopper member; and
       a protruding portion provided at the stem portion and between the first tissue holding surface and the abutting portion, the protruding portion extending in a diameter direction of the stem portion and including a second tissue holding surface formed toward the rearward direction, the second tissue holding surface having an area large enough to hold the living tissue; and an operating member provided on the stopper member and configured to hold the tissue sampling unit when the tissue sampling unit punctures the living tissue.

12. The biopsy tissue sampling treatment instrument according to claim 11, wherein the stopper member is formed of an elastic material and configured to be variable in the external dimension around a longitudinal axis of the tissue sampling unit.

13. The biopsy tissue sampling treatment instrument according to claim 12, wherein the stopper member is disposed so as to allow a separation distance from the puncturing portion to be changed and allows a position which defines an amount of puncture depth of the tissue sampling unit and the protruding portion in the living tissue to be varied.

* * * * *